(12) United States Patent
Seyfried et al.

(10) Patent No.: US 8,293,490 B2
(45) Date of Patent: Oct. 23, 2012

(54) METHOD FOR HIGH SPATIAL RESOLUTION STOCHASTIC EXAMINATION OF A SAMPLE STRUCTURE LABELED WITH A SUBSTANCE

(75) Inventors: Volker Seyfried, Nussloch (DE); Jochen Sieber, Mannheim (DE)

(73) Assignee: Leica Microsystems CMS GmbH, Wetzlar, DE (US)

( * ) Notice: Subject to any disclaimer, the term of this patent is extended or adjusted under 35 U.S.C. 154(b) by 415 days.

(21) Appl. No.: 12/632,639

(22) Filed: Dec. 7, 2009

(65) Prior Publication Data

US 2010/0160613 A1 Jun. 24, 2010

(30) Foreign Application Priority Data

Dec. 22, 2008 (DE) .......................... 10 2008 064 164

(51) Int. Cl.
*G01N 33/53* (2006.01)
*G01N 31/00* (2006.01)
(52) U.S. Cl. ........ 435/7.21; 435/7.1; 436/501; 436/518; 424/9.1; 424/520; 422/50; 530/300; 530/350
(58) Field of Classification Search .................. None
See application file for complete search history.

(56) References Cited

U.S. PATENT DOCUMENTS

2008/0032414 A1 2/2008 Zhuang et al.

FOREIGN PATENT DOCUMENTS

WO 2006127692 11/2006
WO 2007128434 11/2007

OTHER PUBLICATIONS

Manley, Suliana; Gilette, Jennifer M.; Patterson, George H., Shroff, Hari; Hess, Harald F, Betzig, Eric; Lippincott-Schwartz, Jennifer:High-Density Mapping of Single-Molecule Trajectories with Photoactivated Localization Microscopy; Nature Methods; vol. 5 No. 2, Feb. 2008.

*Primary Examiner* — Lisa Cook
(74) *Attorney, Agent, or Firm* — Schlee IP International, P.C.; Alexander R. Schlee

(57) ABSTRACT

A method for high spatial resolution stochastic examination of a biological sample structure labeled with a labeling substance is described. The method comprises providing a biological sample structure; choosing such a labeling substance that has molecules present in a first state and in a second state, and the first and second states differ from one another in at least one photophysical property such that there is sufficient probability that one portion of the molecules of the substance will be in the first state and another portion of the molecules will be in the second state and within which labeling substance a change of the state of the molecules can occur spontaneously between the two states in both directions; and labeling the biological sample structure with the substance.

20 Claims, 2 Drawing Sheets

State A

State B

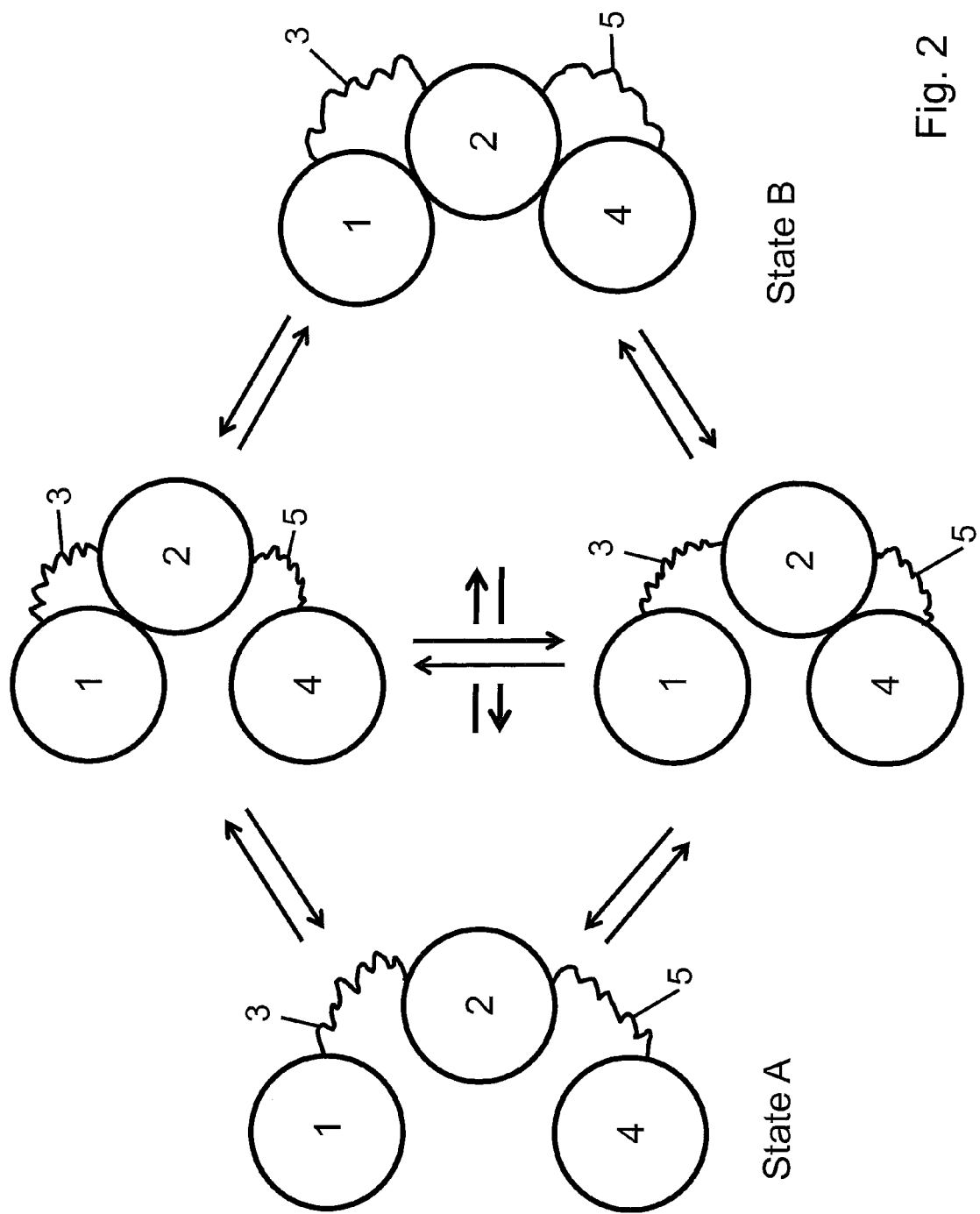

METHOD FOR HIGH SPATIAL RESOLUTION STOCHASTIC EXAMINATION OF A SAMPLE STRUCTURE LABELED WITH A SUBSTANCE

CROSS-REFERENCE TO RELATED APPLICATION

This application claims the priority of the German patent application DE 102008064164.2 having a filing date of Dec. 22, 2008. The entire content of this prior German patent application DE 102008064164.2 is herewith incorporated by reference.

BACKGROUND OF THE INVENTION

The present invention relates to a method for high spatial resolution stochastic examination of a sample structure labeled with a substance, whereby a biological structure is used as the structure labeled with the substance, molecules of the substance may be present in a first state and in a second state, and the first and second states differ from one another in at least one photophysical property.

Methods for high spatial resolution stochastic examination of a sample structure labeled with a substance are known in the art. In this regard, reference is made to WO 2006/127692 A2, US 2008/0032414 A1 and WO 2007/128434 A1, which describe stochastic high-resolution and localization microscopy methods, which are known as PALM, STORM, PALM-IRA and GSDIM, respectively. Moreover, it is known from the journal "Nature Methods", Vol. 5, No. 2, February 2008, pp. 155-157, that photoactivated localization microscopy (PALM) can be performed on living cells, making it possible to track movements of individual particles or molecules. This method is also referred to as sptPALM (single particle tracking PALM).

In all of the known methods for high spatial resolution stochastic examination of a sample structure labeled with a substance, where a biological structure is used as the structure labeled with the substance, molecules of the substance may be present in a first state and in a second state. These first and second states differ from one another in at least one photophysical property. This photophysical property often consists in the ability to fluoresce. In other words, there may be a first fluorescent state and a second non-fluorescent state.

In the known methods, a substance with which a structure of interest is labeled is actively switched between two states. In PALM, PALMIRA or STORM, for example, the substance is switched from a non-fluorescent state to a fluorescent state. This is usually accomplished using light. In this process, care is taken to ensure that only so many molecules of the substance are in the fluorescent state, so that most of the signals that are detected by a microscope having a CCD camera, for example, can be uniquely associated with individual molecules. This is the fundamental idea underlying these stochastic methods, in which a plurality of images are recorded. After determining the centroid of the recorded signals, a high-resolution image is constructed from the centroids by superimposing the plurality of recorded images.

In the GSDIM method, for example, a fluorescent substance is "pumped" into a dark state A, in which it does not fluoresce and from which it may spontaneously return to the initial fluorescent state B. Using a defined illumination, it can be achieved that only a certain amount of molecules fluoresce simultaneously, and can thus be localized. Analogously to the other high-resolution stochastic methods, a high-resolution image can be generated by recording a series of images of signals from single molecules and determining and summing the individual centroids.

All of the previously known methods for high spatial resolution stochastic examination of a sample structure labeled with a substance require active switching between two states. This switching is typically accomplished by light, for example by illumination with a laser. The need for this active switching operation makes the known methods complex.

SUMMARY OF THE INVENTION

It is, therefore, an object of the present invention to provide a method of the above-mentioned type which allows a sample structure labeled with a substance to be examined in a particularly simple manner.

The above object is achieved in accordance with the present invention by the method in question for high spatial resolution stochastic examination of a sample structure labeled with a substance that is further developed and refined by using a substance within which there is sufficient probability that a large enough portion of the molecules will be in the first state and a large enough portion of the molecules will be in the second state, and within which a change can occur spontaneously between the two states in both directions.

DETAILED DESCRIPTION OF THE INVENTION

In accordance with the present invention, it was found that the aforementioned object is achieved in a surprisingly simple manner through suitable selection of the labeling substance. Specifically, to this end, a substance is used in which a change between two suitable states occurs spontaneously. There is no need to activate the substance, or to specifically switch it from one state to another using, for example, a laser. What is important in the use of the substance according to the invention is that both the first and second states be present with sufficient probability. In other words, there is sufficient probability that a large enough portion of the molecules will be intrinsically in the first state, and that a large enough portion of the molecules will be intrinsically in the second state. Ultimately, there is a dynamic equilibrium between the two states, and a change may occur spontaneously between the states.

Such spontaneous changing of states can be elegantly used in stochastic high-resolution and localization microscopy because the spontaneous changes between the states ensure that only a certain number of molecules are in the particular state at a given time. It never happens that all molecules are in the same state at the same time. Thus, here too, as in corresponding methods known heretofore, only a certain amount of molecules are in a state having the desired photophysical property, which may, for example, be a fluorescent state.

The method of the present invention may be referred to as "spontaneous switching localization microscopy or SSLM", in which a substance which spontaneously changes between states is used for labeling the desired structure of a sample. This method is similar to the conventional stochastic localization microscopy methods, except that a substance as described above is used according to the present invention.

The fundamental difference of the present invention from the conventional methods is that the substance does not need to be actively switched from one state to another. Rather, the changing between the two states occurs intrinsically, so that no active switching is needed.

Thus, the present invention provides a method for high spatial resolution stochastic examination of a sample structure labeled with a substance, whereby the labeled structure of the sample can be examined in a particularly simple manner.

A typical method according to the present invention may be implemented to include the following sequence of method steps: Initially, a sample is labeled with the substance or with a tag that binds the substance. Such methods for labeling a sample with a tag that binds the substance are known in the art. In a subsequent step, a series of images may be recorded of a sample. It is important in this context that the amount of the substance that is in a state in which it can emit detectable signals be only so large that a substantial portion of the signals that come from single molecules and are detected with the diffraction-limited resolution of a microscope can still be uniquely associated with the emitting single molecules. In a next step, the centroids of the single molecules may be determined in the images of the series. Finally, a high-resolution image may be constructed from the series of centroid images.

In an advantageous embodiment of the method of the present invention, the molecules of the substance may be present in at least one additional state, all states differing from one another in at least one photophysical property, and there being sufficient probability that a large enough portion of the molecules will be in the first state, a large enough portion of the molecules will be in the second state, and a large enough portion of the molecules will be in the least one additional state, it being possible for a change to occur spontaneously between all states in all directions. In other words, the method of the present invention is not limited to a substance in which only two states exist. Rather, it is also conceivable that three or more states may exist between which changes may occur spontaneously to approximately the same or different extent. A substance having a suitable number of states may be suitably selected depending on the particular application. Specifically, at least one state may be a non-fluorescent state, and at least one other state may be a fluorescent state. However, it would also be possible to use a different photophysical property that distinguishes the respective states.

It is conceivable to use the method of the present invention in applications where different average dwell times of the molecules of the substance in one or in all of the states are advantageous. Depending on the particular application, the dwell time of the molecules in one or several states may be a few microseconds, for example. Longer or shorter dwell times may also be advantageous, depending on the particular application.

As a general principle, the dwell time of the molecules in one or several states, or the rate of change between the states, may be controllable by varying at least one external parameter. Thus, the method may be adapted to the particular sample to be examined.

One very simple approach provides that the at least external parameter is the temperature, an electric field, or light. The dwell time of the molecules in one or several states, or the rate of change between the states, may be variable as a function of the temperature level, the magnitude of the field, or the intensity of the light. In this connection, consideration must be given to the particular application.

Alternatively or additionally, control may be accomplished by interaction with at least one component in the sample or with at least one component in a solution containing the structure. To this end, suitable components may be added into the sample or into the solution as desired to achieve the desired control. Further alternatively or additionally, control may be accomplished by changing the pH value of a solution containing the structure.

Furthermore, it is advantageous if control is accomplished by changing the concentration and/or a property of at least one component in the sample or of at least one component in a solution containing the structure. Moreover, control may be accomplished by replacing a solvent or by changing a property of the solvent in a solution containing the structure. Finally, control may be accomplished by interaction with a local environment, preferably with a surface or with a predeterminable state of a predeterminable structure in the sample.

With regard to the aforementioned ways of achieving control, it should be noted that the above listing is not meant to be exhaustive. It is perfectly possible to implement other ways of controlling the dwell time or the rate of change. In all cases, with respect to the control options, consideration must be given to the particular application. In principle, the rate of change between the states, or the dwell time in the states, may also be dependent on the density of the substance in the sample. Depending on the particular application, a higher or lower density is to be selected for the substance in the sample. Ultimately, depending on the density of the substance in the sample, different rates of change between the states may be advantageous, so that it is useful to control the rate of change in a suitable manner.

In a specific embodiment, the substance may include at least two constituents, and the constituents may interact with each other in one state while in another state they may not. The two states may exist in a dynamic equilibrium. Here too, the dwell time of the constituents in the state with interaction and in the state without interaction may be controllable as described above. Also, the rate of change between the states may be controllable by varying at least one external parameter as described above. In this case, too, where the substance includes at least two constituents, a photophysical property in the state in which interaction is possible may differ from the photophysical property in the other state.

Moreover, specifically, a desired signal may be obtained from the substance only in the case where the constituents do not interact with each other. Alternatively, depending on the particular application, a desired signal may only be obtained from the substance when the constituents do interact with each other.

An example in which a signal is only obtained when the constituents do not interact with each other may be what is known as "quenching", i.e., reversible fluorescence quenching by a quencher. An example in which a suitable signal is only obtained when the constituents do interact with each other may be given in a case where the constituents are the donor and the acceptor of a FRET (fluorescence resonance energy transfer) pair, the desired signal being the fluorescence of the acceptor.

The constituents may be connected by a linker, and the dwell time of the constituents in one of the states, or the rate of change between the states, may be controllable by the binding of a component to the linker, by an ion concentration in a solution containing the structure, or by the pH value. Furthermore, the equilibrium between the two states may be controlled by the temperature. Depending on the particular application, the equilibrium may be advantageously shifted in such a way that either the one or the other state is present in a larger proportion and with greater probability.

For example, in the case of Chameleon, a Ca2+ sensor composed of a FRET pair of two fluorescent proteins bound by a linker, the conformation, and thus the FRET efficiency and the intensity of the acceptor signal, may be controlled via the Ca2+ concentration.

In another specific embodiment, the substance or a substance complex, may be present in two conformations or quaternary structures which are present in a dynamic equilibrium and fluoresce, for example, only in one of these states. The substance or substance complex used may, for example, be a protein or a protein complex. The equilibrium, i.e., the dwell time or the rate of change, may be controlled in the manner described above.

In order to provide a particularly efficient examination method, a plurality of sample structures labeled with different substances may be simultaneously or sequentially examined by the same detector or by different detectors and be differentiated on the basis of different properties of the respective detected signals so as to obtain a high-resolution image of a plurality of structures. The different properties may include, for example, different emission and excitation spectra.

Efficient and specific illumination of the sample may be accomplished using SPIM (Selective Plane Illumination Microscopy) illumination, TIRF (Total Internal Reflection Fluorescence) illumination, or wide-field illumination. In addition to performing the detection using one camera, it may be advantageous to perform the detection using a plurality of cameras which also allow 3D information to be obtained in high-resolution. With regard to the analysis of the data obtained, it is possible to use conventional analysis methods, especially those allowing 3D representations to be obtained via the shape and magnitude of the detected signals.

Further advantageously, the method of the present invention may be used in a method analogous to the one known as sptPALM (single particle tracking PALM). In this case, in place of generating a high-resolution image from the series of centroid images, it is possible to analyze movements of the respective single molecules between the images. Analogously to sptPALM, the advantage over conventional single particle tracking methods is the ability to always read out different molecules that are currently in the state in which they emit the detectable signal. Thus, it is possible, for example, to obtain a much better statistic for a cell than would be possible using conventional single particle tracking methods. The method of the present invention has the advantage that no active switching between the states is needed.

The teaching of the present invention may be advantageously embodied and refined in various ways. In this regard, reference is made, on the one hand, to the claims that are subordinate to claim 1 and, on the other hand, to the following description of preferred exemplary embodiments of the invention which makes reference to the drawing. In conjunction with the explanation of the preferred exemplary embodiments of the present invention with reference to the drawing, an explanation is also given of generally preferred embodiments and refinements of the teaching.

BRIEF DESCRIPTION OF THE DRAWINGS

FIG. 2 is a schematic view of another exemplary embodiment of a suitable substance, said substance including three constituents connected by linkers.

DETAILED DESCRIPTION OF THE DRAWINGS

Figure 1:
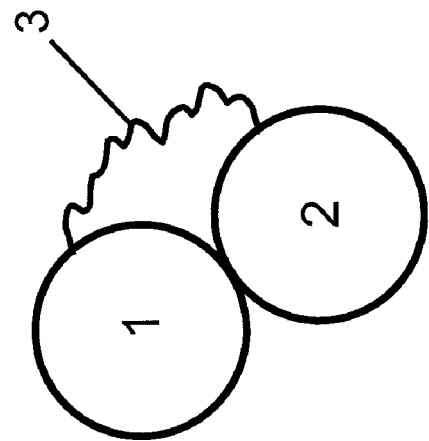
FIG. 1 is a schematic view of an exemplary embodiment of a substance that can be used in the method of the present invention, said substance including two constituents connected by a linker.
Figure 1:
Figure 1:
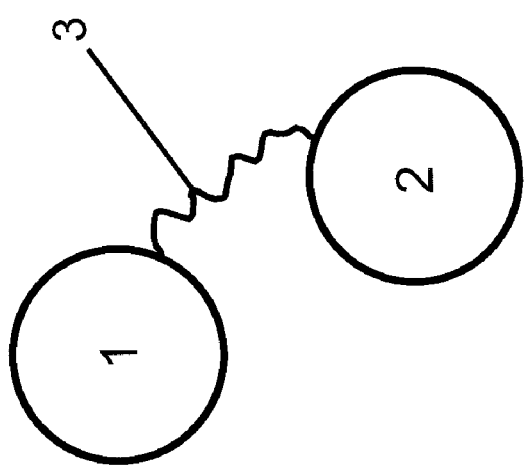

In a schematic representation, FIG. 1 shows a substance that can be used in an exemplary embodiment of the method of the present invention, said substance including two constituents 1 and 2 which are connected to each other by a flexible linker 3. The substance can be present in two states A and B, which exist in a dynamic equilibrium. Constituents 1 and 2 can interact with each other in one of these states while in the other they cannot.

In this connection, a signal may only be obtained when the constituents do not interact with each other or when they do interact with each other. The states A and B exist with controllable probabilities, it being possible for a change to occur spontaneously between the two states in both directions.

In a schematic representation, FIG. 2 shows another substance which can be used in the method of the present invention. The substance shown in FIG. 2 includes three constituents 1, 2 and 4, constituents 1 and 2 being connected to each other by a linker 3 and constituents 2 and 4 being connected to each other by a linker 5.

FIG. 2 shows intermediate states between the states A and B. These intermediate states can also occur spontaneously. In the case of the intermediate state shown in the upper portion of FIG. 2, constituents 1 and 2 are adjacent or bound to each other, while in the case of the intermediate state shown in the lower portion of FIG. 2, constituents 2 and 4 are adjacent or bound to each other. In state A, none of the constituents 1, 2 or 4 are adjacent to each other, whereas in state B, all of the constituents 1, 2 and 4 are adjacent to each other or bound, respectively.

In the case of the exemplary embodiment of a substance illustrated in FIG. 2, the dwell time of constituents 1, 2 and 4 in states A and B, or the rate of change between states A and B, is also controllable.

Finally, it should be emphasized that the exemplary embodiments discussed above are merely intended to illustrate the claimed teaching, but not to limit it to such embodiments.

LIST OF REFERENCE NUMERALS 1 constituent
2 constituent
3 linker
4 constituent
5 linker
A state
B state

What is claimed is:

1. A method for high spatial resolution stochastic examination of a biological sample structure labeled with a labeling substance, comprising:
   providing the biological sample structure;
   choosing such a labeling substance that has molecules present in a first state and in a second state, and the first and second states differ from one another in at least one photophysical property such that there is sufficient probability that one portion of the molecules of the substance will be in the first state and another portion of the molecules will be in the second state and within which labeling substance a change of the state of the molecules can occur spontaneously between the two states in both directions; and
   labeling the biological sample structure with the substance.

2. The method according to claim 1, comprising choosing such a labeling substance that has molecules present in at least one additional state in addition to the first and second states, wherein all states differ from one another in at least one photophysical property such that there is sufficient probability that a portion of the molecules will be in the first state, a portion of the molecules will be in the second state, and a portion of the molecules will be in the at least one additional state, it being possible for a change to occur spontaneously between all states in all directions.

3. The method according to claim 1, comprising choosing the labeling substance such that at least one of the first and second states is a non-fluorescent state, and at least one of the second and first states is a fluorescent state.

4. The method according to claim 2, comprising choosing the labeling substance such that at least one of the first, second and additional states is a non-fluorescent state, and at least one of the additional, second and first states is a fluorescent state.

5. The method according to claim 1, comprising choosing the labeling substance such that the dwell time of the molecules in the first or second state is a few microseconds.

6. The method according to claim 2, comprising choosing the labeling substance such that the dwell time of the molecules in at least one of the first and second and additional states is a few microseconds.

7. The method according to claim 1, comprising choosing the labeling substance such that a dwell time of the molecules in at least one state is controllable by varying at least one external parameter.

8. The method according to claim 1, comprising choosing the labeling substance such that the rate of change between the states is controllable by varying at least one external parameter.

9. The method according to claim 7, comprising choosing the labeling substance such that the at least at least one external parameter is at least one of the temperature, electric field, and light.

10. The method according to claim 8, comprising choosing the labeling substance such that the at least one external parameter is at least one of the temperature, electric field, and light.

11. The method according to claim 7, comprising changing the concentration of at least one of at least one component in the biological sample structure and of at least one component in a solution containing the biological sample structure.

12. The method according to claim 8, comprising changing the concentration of at least one of at least one component in the biological sample structure and of at least one component in a solution containing the biological sample structure.

13. The method according to claim 7, comprising at least one of replacing a solvent and changing a property of the solvent in a solution containing the biological sample structure.

14. The method according to claim 1, comprising providing at least one of a rate of change between the first and second states and the dwell time in the first and second states dependent on the density of the substance in the sample.

15. The method according to claim 1, comprising choosing the labeling substance such that it includes at least two constituents that can interact with each other in one of the first and second state while in the other second or first state they cannot interact.

16. The method according to claim 15, comprising choosing the labeling substance such that a photophysical property in the first or second state in which interaction is possible differs from the photophysical property in the other second or first state where interaction is not possible.

17. The method according to claim 16, comprising choosing the labeling substance such that the constituents are the donor and the acceptor of a FRET pair; and the desired signal is the fluorescence of the acceptor.

18. The method according to claim 17, comprising choosing the labeling substance such that the constituents are connected by a linker; and
at least one of the dwell time of the constituents in one of the first and the second states and of the rate of change between the states is controllable by at least one of the binding of a component to the linker, an ion concentration in a solution containing the biological sample structure, and the pH value.

19. The method according to claim 1, comprising choosing the labeling substance or a substance complex as a protein or a protein complex that can be present in two conformations or quaternary structures which are present in a dynamic equilibrium and fluoresce only in one of these states.

20. The method according to claim 1, comprising using the method analogously to a method known as sptPALM (single particle tracking PALM).

* * * * *